United States Patent [19]

Sieklucki et al.

[11] 4,179,159

[45] Dec. 18, 1979

[54] URINARY DRAINAGE BAG SUPPORT

[75] Inventors: James F. Sieklucki, 1510 Spruce Dr., Kalamazoo, Mich. 49008; Ralph Veld, Jr., Kalamazoo, Mich.

[73] Assignee: James F. Sieklucki, Kalamazoo, Mich.

[21] Appl. No.: 886,068

[22] Filed: Mar. 13, 1978

[51] Int. Cl.[2] ........................... A47C 7/62; A61F 5/44

[52] U.S. Cl. ........................................ 297/192; 5/508; 128/275; 297/DIG. 4

[58] Field of Search ................. 297/188, DIG. 4, 189, 297/192, 193; 128/295, 275; 248/311.1 R, 95, 316 D, 99, 100, 101; 5/317, 92; 150/52 E

[56] References Cited

U.S. PATENT DOCUMENTS

| | | | |
|---|---|---|---|
| 469,061 | 2/1892 | Henning et al. | 248/99 X |
| 792,128 | 6/1905 | Haverstick | 5/317 R |
| 1,927,751 | 9/1933 | Mensi | 150/52 E |
| 2,163,759 | 6/1939 | McCann | 297/192 |
| 3,081,464 | 3/1963 | Lochner | 5/92 |
| 3,548,827 | 12/1970 | Abel | 128/275 |
| 3,896,809 | 7/1975 | Samuel et al. | 128/275 |
| 4,085,755 | 4/1978 | Burrage | 128/295 |

*Primary Examiner*—James T. McCall
*Attorney, Agent, or Firm*—Blanchard, Flynn, Thiel, Boutell & Tanis

[57] ABSTRACT

A bracket fixable to a side rail of a patient support, such as a wheelchair, supports a horizontally pivoted arm movable from a use position beneath the front edge portion of the seat to a rearwardly extending stowed position. The arm carries an envelope which opens upward to receive a conventional urinary drainage bag for connection through a drain tube to a catheterized patient on the seat. When installed on a conventional transversely collapsible, X-braced wheelchair, rearward pivoting of the arm substantially into parallelism with the side rails of the chair permits conventional transverse collapsing of the chair.

12 Claims, 7 Drawing Figures

FIG. 1
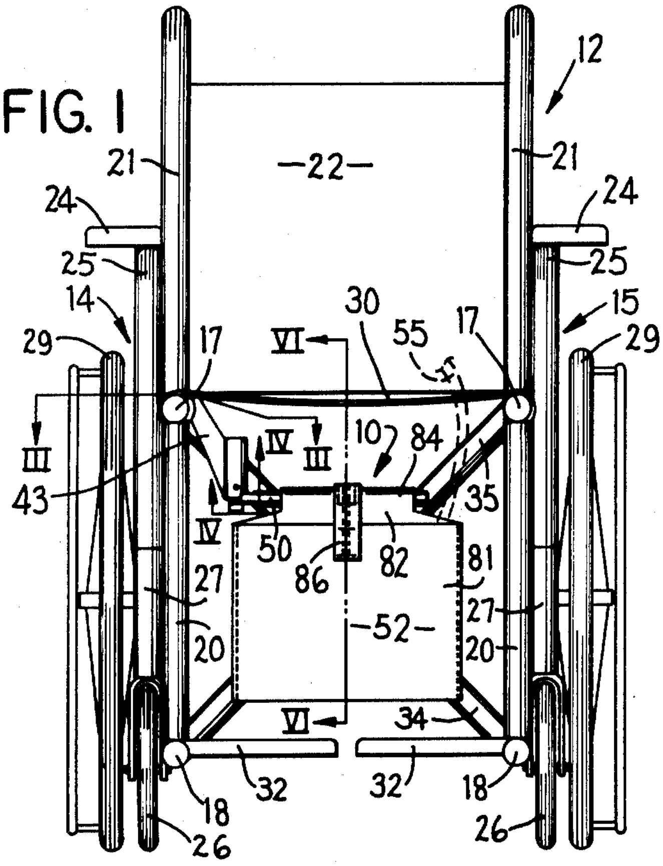
FIG. 2
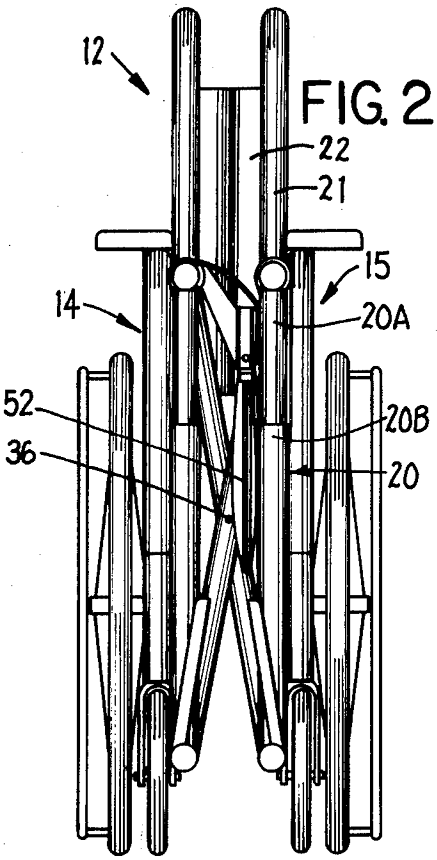
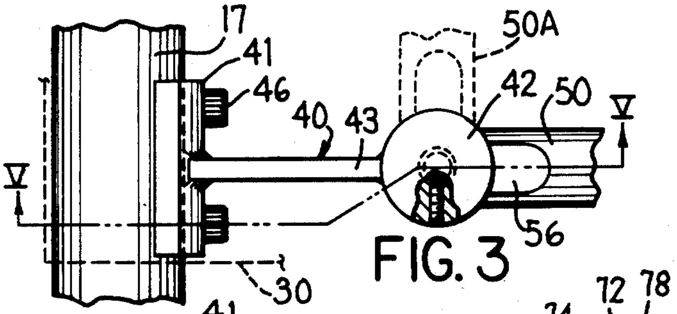
FIG. 3
FIG. 4
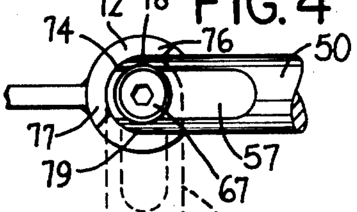
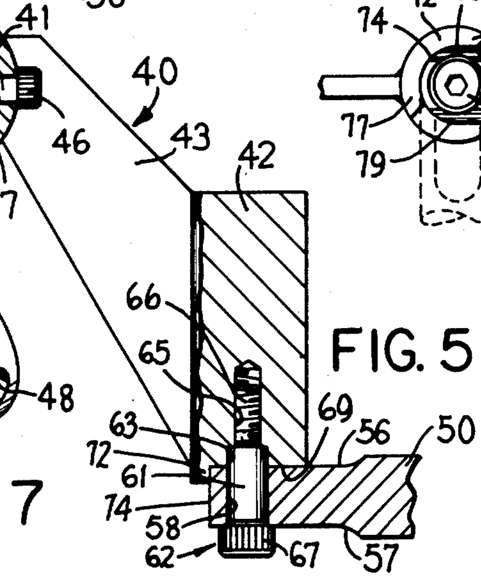
FIG. 5
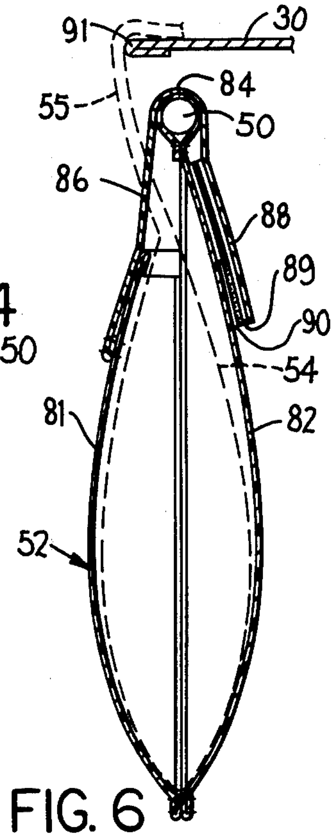
FIG. 6
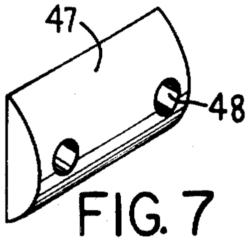
FIG. 7

URINARY DRAINAGE BAG SUPPORT

FIELD OF THE INVENTION

This invention relates to a urinary drainage bag support mountable on a patient support, particularly a transversely collapsible wheelchair.

BACKGROUND OF THE INVENTION

Patients unable to control the natural flow of urine may conventionally be equipped with a catheter in turn connected by a drain tube to a urinary drainage bag. A typical commercial drainage bag is a flat, pouchlike container of flexible sheet plastic material. The connected drain tube is typically about four feet in length, for example sufficient to reach from the catheterized patient on a bed to a drainage bag located beneath the bed. Typically, the drainage bag incorporates a pair of support grommets along its upper edge for support by a cord or hooked wire from a convenient part of the bed frame.

When the patient is moved to a wheelchair, the drainage bag has often been suspended on the side of the wheelchair. However, this may result in entanglement of the bag or drain tube with the adjacent chair wheel, or furniture past which the chair moves, with a consequent possibility of rupturing or disconnecting of the bag or tube and consequent spillage of the contents thereof. Further, contact with the wheel tends to transfer dirt and the like from the floor to the surface of the bag and tube, while entanglement with the wheel raises the possibility of constriction of the tube sufficient to cause backup to urine to the bladder, thereby increasing the risk of urinary infection in the patient.

In an attempt to avoid constriction of the drain tube by a chair wheel, U.S. Pat. No. 3 896 809 (Samuel) discloses suspending the urinary drainage bag by the usual cord or string but from a hook at the rear face of the back of the wheelchair, such that the bag lies to the rear of and well below the seat of the wheelchair. While the drainage bag is thus spaced in between the main wheels of the chair, the patented system raises some additional problems.

More particularly, positioning of the drainage bag below and to the rear of the seat tends to place it in the way of the feet and lower legs of an attendant pushing the wheelchair, making it easy to accidentally kick and thereby contaminate the drainage bag with dirt from the floor, or even rupture the drainage bag with consequent risk of leakage. Also, as the patent shows, the drainage bag conventionally is provided with a short outlet tube mounted low in the bag, by which the drainage bag can be emptied. With the bag mounted so low on the wheelchair and in such close proximity to the floor and to the shoes of an attendant, there appears to be substantial risk of dirt or other contaminants settling on this outlet tube and thereby enhancing the possibility of infiltration of the drainage and drain tube by undesirable bacterial agents.

Further, the patented system avoids placing the drain tube near the chair wheels by extending the drain tube from the rear mounted bag along a path beneath the chair seat and thus up and over the front of the chair seat to the catheterized patient. As a practical matter, transfer of the patient from wheelchair to bed or vice versa will normally be done by disconnecting and then reconnecting the patient to the drainage bag, normally at the juncture between the catheter and drainage tube, to avoid having to move the drainage bag and its support cord forwardly, or rearwardly, beneath the wheelchair seat. Not only is such transfer cumbersome at best, it is virtually impossible in modern transversely collapsible wheelchairs with cross or X-bracing or other structural elements beneath the wheelchair seat as may block passage of the drainage bag therebeneath. Even without obstructions beneath the wheelchair seat, the added weight of an other than entirely empty bag would tend to discourage an attentant from attempting to pass the bag and drain tube beneath the wheelchair seat. Disconnection of the patient from the bag avoids this problem but creates another, namely increasing the risk of urinary infection in the patient due to disconnection and reconnection of the drain tube. The risk of infection is additionally enhanced by the need to thread the drain tube through the cross bracing or other under seat structure of the wheelchair, once the bag has been installed at the rear of the seat, in order to reconnect same to the patient.

The prior art arrangements above-discussed, in addition, may tend to cause embarrassment of some patients by positioning the drainage bag itself, without any covering, in a highly visible position on the wheelchair.

Accordingly, the objects of this invention include provision of:

1. A urinary drainage bag support securable to patient support furniture, such as beds and chairs.

2. A support, as aforesaid, particularly usable in combination with wheelchairs for supporting a urinary drainage bag well out of the way of and safe from contact from the wheels of the chair and the feet of an attendant pushing the chair.

3. A support, as aforesaid, mountable beneath the front edge of the seat of a wheelchair for supporting a urinary drainage bag beneath and near the catheter of a catheterized patient, and ahead of the usual cross bracing on transversely collapsible wheelchairs.

4. A support, as aforesaid, pivotally adjustable substantially horizontally for swinging the supported urinary drainage bag from a use position extending transversely across the front of the wheelchair behind the legs of the patient, to a stowed position extending longitudinally of the chair and in non-interferring relation with collapsible cross bracing below the level of the chair seat.

5. A support, as aforesaid, including a portion substantially completely enclosing the urinary drainage bag to protect same from contamination by environmental dirt or the like and from being ripped or cut by contact with parts of the chair or items in the path thereof, which supports the drainage bag securely without recourse to pendent support of the bag by conventional cords, hooks or the like.

6. A support, as aforesaid, by which the catheterized patient, drainage tube and bag may be installed in, or removed from, the wheelchair as a unit and without need for disconnection as between the catheterized patient, drain tube and bag, and without need for threading the bag and/or tube through underseat bracing or the like of the wheelchair, for easier and quicker installation or removal of the patient from the chair, while minimizing risk of urinary infection in the course of transferring the patient into or out of his wheelchair, and which permits the patient himself to readily install, use, and remove the drainage bag and drain tube with respect to the wheelchair.

7. A support, as aforesaid, which encloses the drainage bag and locates the drainage bag and drain tube beneath the front part of the wheelchair seat and immediately behind the patient's legs, so as to make as inconspicuous as possible the presence of the bag and tube and thereby reduce to a minimum any embarrassment of the patient as to the appearance to others of the urinary drainage equipment.

8. A support, as aforesaid, readily adaptable to secure mounting on chair side frame members of differing cross sectional shape.

Other objects and purposes of this invention will be apparent to persons acquainted with apparatus of this general type upon reading the following specification and inspecting the accompanying drawings.

SUMMARY OF THE INVENTION

The objects and purposes of the invention are met by providing a urinary drainage bag support in which a bracket fixable to the side rail of a chair, extends transversely in cantilevered relation therefrom beneath the seat of the chair. An arm extends substantially horizontally from the bracket and is pivoted thereon for movement from a transversely extending use position to a longitudinally stowed position substantially parallel to the chair side member. An envelope supported on the arm and pivotable therewith receives a urinary drainage bag.

BRIEF DESCRIPTION OF THE DRAWINGS

FIG. 1 is a front elevational view of a wheelchair and an attached urinary drainage bag support according to the present invention, shown in a position of use.

FIG. 2 is a view similar to FIG. 1 but with the wheelchair transversely collapsed and the drainage bag support in its stowed position.

FIG. 3 is a fragmentary, enlarged, partially broken view substantially as taken on the line III—III of FIG. 1.

FIG. 4 is an enlarged fragmentary view substantially taken on the line IV—IV of FIG. 1.

FIG. 5 is a sectional view substantially taken on the line V—V of FIG. 3 but with a modified chair rail attachment shown.

FIG. 6 is an enlarged cross sectional view substantially taken on the line VI—VI of FIG. 1.

FIG. 7 is an enlarged pictorial view of the mounting adapter of FIG. 5.

DETAILED DESCRIPTION

FIG. 1 illustrates a preferred embodiment of the invention in which a urinary drainage bag support 10 is secured to a conventional wheelchair 12.

While the drainage bag support 10 is mountable on structures other than wheelchairs like that illustrated at 12, such as beds, stationary chairs, and the like, disclosure of the inventive support in combination with a wheelchair, particularly a transversely collapsible wheelchair as shown at 12 in FIGS. 1 and 2, more fully illustrates the advantages of the invention.

Wheelchair 12 here comprises transversely opposed side frames 14 and 15. The side frames have opposed, longitudinally extending upper rail members 17, longitudinally extending lower rail members 18, front uprights 20 adjoining the front ends of respective rail members 17 and 18, and rear uprights connecting the rear ends of respective rail members 17 and 18 and here extending upward at 21 to support the flexible, folding back panel 22 of chair 12. Longitudinally extending arms 24 are carried by upstanding front members 25 and rear members (not shown) fixed to the side frames 14 and 15. Small front caster wheels 26 are pivoted with respect to upstanding caster pin housings 27 suitably fixed with respect to the front uprights 20 of the side frames 14 and 15. Large rear wheels 29 are rotatably fixed to the outward facing sides of the side frames 14 and 15. In the particular embodiment shown, a flexible folding seat panel 30 is fixed at its side edges to the upper frame members 17. Pivotable foot rests 32 mount on forward extensions of bottom rail members 18. In the preferred embodiment shown, chair 12 is transversely collapsible from its use position of FIG. 1 to its collapsed, or stowage, position of FIG. 2. To this end, the chair includes an X-brace defined by cross members 34 and 35 which overlap and are pivotally interconnected intermediate their ends, at 36 (FIG. 2). In the particular embodiment shown, folding and unfolding of the chair between its FIG. 1 and FIG. 2 positions is permitted by use of front and back uprights 20, 21 each with telescoping upper and lower sections, as generally indicated at 20A and 20B of the right front upright of FIG. 2. Typically the X-brace 34, 35 is located beneath the rear portion of seat panel 30, normally beneath the rearmost one-third of the seat panel. The wheelchair 12 is thus conventional and requires no further description.

The drainage bag support 10 comprises a bracket 40. The bracket 40 is of rigid construction, including an attachment portion 41 rigidly securable to the wheelchair, and a pivot portion 42 spaced in cantilevered fashion from attachment portion 41 by a leg 43.

Attachment portion 41 preferably takes the form of a longitudinally extending shell securable to the inner side face of a longitudinal rail member of the chair beneath seat panel 30. In the particular embodiment shown, the shell 41 is conveniently attached to the leftward rail member 17 which in the particular wheelchair shown, also serves to support seat panel 30. Many modern wheelchairs are constructed of tubular steel frame members which are frequently of circular cross section. To permit close fitting securement of shell 41 to such wheelchairs, shell 41 is of semicircular cross section, as seen in FIG. 5, and hence will fit in substantially full area contact against the side of the circular cross section rail 17 of FIGS. 1 and 3. Shell 41 is rigidly fixed to rail member 17 by any convenient means, such as welding, or as here shown, by means of self-tapping screws 46 extending through suitable holes in shell 41 and threadedly engaging rail 17.

To permit a bracket 40 employing a semicircular shell 41 to be used with a square or rectangular cross section rail member, as illustrated for example with respect to tubular steel rail member 17' of FIG. 5, an adapter 47 (FIGS. 5 and 7) of steel or the like, is interposable between the shell 41 and the opposed side face of rail member 17'. Adapter 47 is of uniform cross section with a curved rightward face for full area contact with the concave shell 41 and a flat face on the other side for full area contact with the side of rail member 17'. Holes 48 in adapter 47 permit the passage of screws 46 therethrough to secure the bracket to the rail member.

The drainage bag support 10 further includes a substantially horizontal arm 50 pivotally supported on pivot portion 42 of bracket 40 and which in turn removably supports an envelope 52 pendently therefrom for supporting therewithin a urinary drainage bag indicated in broken lines at 54 in FIG. 6.

The envelope 52 is spaced below the seat panel 30 to provide a vertical drop between the catheterized patient on the seat panel 30 and the drainage bag to be located within envelope 52. On the other hand, envelope 52 is preferably spaced somewhat above footrests 32, to space same well above dirt or other foreign material on the floor or roadway along which the wheelchair may be moved. Envelope 52 is preferably evenly spaced transversely between wheels 29 of the wheelchair, as seen in FIG. 1, to avoid contact or entanglement with the wheels by envelope 52 or a drain tube (indicated in broken lines at 55 in FIGS. 1 and 6) extending between a patient on the seat panel 30 and a drainage bag 54 in envelope 52.

To these ends, leg 43 of bracket 40 is angled transversely inwardly and downwardly from rail member 17 (or 17') as seen in FIGS. 1 and 5. Pivot portion 42 of bracket 40 here comprises an upstanding cylindrical member of circular cross section. Leg 43 is conveniently of steel plate oriented to face forward and rearward and preferably fixed by welding at its ends to shell 41 and cylindrical member 42.

Arm 50 is preferably formed as a rigid rod, conveniently of circular cross section. The pivoted leftward end of rod 50 has flats 56, 57 on its upper and lower sides, respectively, and a vertical bore 58 (FIG. 5) which here upwardly receives therethrough the shank 61 of a shoulder bolt 62 by which arm 50 is pivotally supported by bracket 40. More particularly, the lower end of cylindrical member 42 of the bracket carries a preferably coaxial downwardly opening bore recessed at 63 and threaded at 65 to receive upwardly thereinto respective shank and threaded portions 61 and 66 of shoulder bolt 62. A radially enlarged head 67 on shoulder bolt 62 pendently retains arm 50 on cylindrical bracket member 42. With the shoulder bolt threaded into bore portion 65 sufficient to bottom shank 61 in recess 63, there is sufficient clearance between head 67 and the bottom surface 69 of cylindrical member 42 as to permit free pivoting, in a substantially horizontal plane, of arm 50.

To restrain pivoting of arm 50 to a substantially 90° sector bounded by the transverse use position shown in FIG. 1 and the rearwardly extending stowed position shown in FIG. 2 (and in dotted lines at 50A in FIG. 3), a semicircular skirt 72 depends (preferably integrally) from bracket pivot portion 42. The skirt 72 is formed as a downward extension of the side wall of cylindrical portion 42 and, as seen in FIG. 4, extends circumferentially through somewhat more than 90° and has an inward facing surface in opposed clearance relation with a correspondingly rounded cylindrical end surface 74 of arm 50. Circumferentially short end extensions 76 and 77 extend circumferentially from skirt 72 and, by bearing on the opposed side surface 78 or 79, respectively, of rod 50 limit pivotal motion of arm 50 as aforementioned.

Envelope 52 is constructed of a tough, flexible, and easily cleanable material such as sheet vinyl or the like. Envelope 52 comprises a substantially rectangular front panel 81 (FIG. 6) fixed along its side and bottom edges (as by stitching) to an upstanding substantially rectangular back panel 82 to form an envelope open along the upper edge of front panel 81 for receiving a conventional urinary drainage bag 54 therein. The top of rear panel 82 extends upward beyond front panel 81 and terminates in an upper edge portion which is folded over upon itself and edge secured to form a horizontal tube at 84 slidably receivable over the arm 50 to support the envelope therefrom. In the preferred embodiment shown, the width of back panel 82 is reduced near its upper end, making the tube 84 only about one-half the width of the lower portion of envelope 52. This permits the envelope 52 to be installed on and removed from arm 50, with the latter in its use position of FIG. 1, despite the adjacent side frame structure of the wheelchair, for example by a relatively easy bending or curving of envelope 52 yet to form a substantially vertically extending forwardly concave shape.

In normal operation, the envelope 52 is supported on arm 50 in its substantially centered position shown in FIG. 1. Once positioned, the envelope 52 tends to maintain its position lengthwise of arm 50 by friction.

The bracket 40 and hence arm 50 are positioned, as seen in FIG. 3, beneath the front edge portion of seat panel 30, the arm 50 being of length that when pivoted rearwardly to its position 50A, it preferably terminates short of the plane of chair cross members 34 and 35. If desired, bag 52 may be shifted leftwardly along arm 50 from its centered position shown preparatory to pivoting the arm rearwardly to its stowed position 50A, to avoid any substantial interference between envelope 52 and chair cross members 34 and 35. However, this will normally not be necessary in view of the flexibility of envelope 52 which will tend to bend or otherwise deform to give way to the cross members 34 and 35 as the arm pivots rearwardly to its stowed position 50A.

Envelope 52 includes a closure strip 86, preferably centered transversely on the envelope 52 as shown in FIG. 1 and arranged to adjustably close over the top of a drainage bag 54 within envelope 52, to permit reception of bags of different sizes within envelope 52. Closure strip 86 when secured as shown prevents the upper edge portion of front panel 81 from falling forward, under the press of a partially or fully filled urinary drainage bag therein, so as to prevent tipping of the drainage bag forwardly out of the envelope or against the legs of the patient occupying the chair. In addition closure strip 86 is rapidly releasable and engageable to any desired effective length within its range. To these ends, strip 86 is secured, as by sewing, to the upper central portion of front panel 81 and, when in its closed position shown, extends upward over the top of tube 84 and arm 50 to a rearward latchable end portion 88 adjustable to the back side of back panel 82 by elongate complementary fabric hook and loop strips 89 and 90 preferably secured to strip end portion 88 and panel 82 by sewing, such hook and loop strips being commercially available under the trade name Velcro.

With bracket 40, arm 50 and envelope 52 in a use position shown in FIGS. 3 and 6, below the front edge 91 of seat panel 30, the drain tube 55, interconnecting a catheterized patient seated on panel 30 with a urinary drainage bag 54 pocketed within envelope 82, leads directly over the front edge 91 of seat 30. Accordingly, the patient, drain tube 55 and drainage bag 54 can, without disconnection one from the other, be removed from the wheelchair, simply by opening of closure strip 86 (by pulling end 88 thereof up and forwardly) to release drainage bag 54.

With the patient removed, the chair and drainage bag support structure can be collapsed for storage. More particularly, arm 50 with envelope 52 supported thereon is normally first swung rearward to its position 50A whereafter chair 12 can be transversely collapsed from its FIG. 1 to FIG. 2 position, wherein the side frames 14 and 15 loosely sandwich arm 50 and envelope 52 therebetween. Chair 12 and bag support 10 are opened for use and a patient with connected drain tube 55 and drainage bag 54 are installed thereon substantially by a reversal of the foregoing steps.

Where the drain tube 55 is of length substantially exceeding that required to extend from the envelope 52 to the patient seated on panel 30, the excessive length central portion of tube 55 may be laid in one or more S patterns transversely of the chair atop the drainage bag 54 in envelope 52, and held in place by closure strip 86 passing over the top thereof.

If desired, a drainage support 10 may be provided on another piece of the patient's furniture.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. In combination with a conventional wheelchair of the kind having a transversely collapsible seat, spaced opposed side frames including opposed side rail members and connected for transverse movement toward and away from each other between a full width use position, for supporting a person on said chair, and a reduced width nonuse position, said chair having a seat, a said rail member extending longitudinally adjacent one side of said seat and being accessible from below said seat, a urinary drainage bag support, comprising:

a bracket fixed to said rail member and extending in transversely cantilevered relation therefrom beneath said seat;

an arm extending substantially horizontally from said bracket and pivoted thereon for movement from a transversely extending use position to a longitudinal stowed position substantially parallel to said rail member;

an envelope, for receiving a urinary drainage bag therein, supported on said arm and pivotable therewith between said use and stowed positions, said arm in its use position extending transversely between said side frames and supporting said envelope in forward facing orientation beneath said seat, said stowed position of said arm being angled rearward through about a right angle from said use position of said arm.

2. The apparatus of claim 1, in which said bracket, and in their use positions said arm and envelope, lie below the front edge of said seat, said envelope having an upward facing opening for entry of a urinary drainage bag, whereby a catheterized patient and his urinary drainage bag can be installed in said seat and envelope respectively, and also removed therefrom, without need to disconnect a drain tube coupling said patient to said urinary drainage bag.

3. In combination with a chair having a seat and a rail member extending longitudinally adjacent one side of said seat and accessible from below said seat, a urinary drainage bag support, comprising:

a bracket fixed to said rail member and extending in transversely cantilivered relation therefrom beneath said seat;

an arm extending substantially horizontally fron said bracket and pivoted thereon for movement from a transversely extending use position to a longitudinal stowed position substantially parallel to said rail member;

an envelope, for receiving a urinary drainage bag therein, supported on said arm and pivotable therewith between said use and stowed positions, said envelope comprising front and rear panels continuously connected along their bottom and opposite side edges to provide a pouchlike container open at the top for receiving a urinary drainage bag, said rear panel extending upward beyond said front panel and having an upper edge portion folded over upon itself and edge-secured to form an open ended horizontal tube extending axially along the upper edge of said envelope and slidably telescoped on said arm thereby cantilevering said envelope from said bracket substantially in coplanar relation with said arm, and including a closure strip extending from the central upper edge portion of said front panel to the upper portion of said rear panel to limit forward bulging of said front panel by a filled urinary drainage bag while permitting free entry into the envelope of the drainage bag input hose.

4. The apparatus of claim 3, in which said closure strip extends over the top of said tube to engage the rear face of said rear panel and including multiple hook-and-loop releasable connecter pads extending along one end of said strip and the opposed surface of said envelope for rapid and adjustable securement of the open upper end of said envelope by said strip.

5. In combination with a chair having a seat and rail member extending longitudinally adjacent one side of said seat and accessible from below said seat, a urinary drainage bag support, comprising:

a bracket fixed to said rail member and extending in transversely cantilevered relation therefrom beneath said seat;

an arm extending substantially horizontally from said bracket and pivoted thereon for movement from a transversely extending use position to a longitudinal stowed position substantially parallel to said rail member;

an envelope, for receiving a urinary drainage bag therein, supported on said arm and pivotable therewith between said use and stowed positions, said bracket and arm having respective axially opposed end portions and including a substantially vertically extending pivot pin pivotally securing said arm on said bracket, said end portion of said bracket having axially protruding skirt means disposed along the path of pivotal movement of said arm for limiting the swing of said arm to about a quarter circle.

6. The apparatus of claim 5, in which the pivoted end of said arm has a flattened top surface and a rounded end surface, said flat surface of said arm opposing the corresponding radial surface at the bottom of the opposed end portion of said bracket, said arm having a hole therethrough aligned with a stepped hole in said opposed bracket end portion, wherein the remote end of said hole in said bracket end portion is threaded, said pivot pin comprising a shoulder bolt pivotally received through said hole in said arm and threadedly engaging said hole in said bracket end portion, said shoulder bolt seating against an axially opposing surface in said hole in said bracket end portion and being headed to axially retain said arm in supported relation beneath said bracket end portion yet permit pivoting out of said arm thereon, and including means positively securing said shoulder bolt to said bracket end portion.

7. The apparatus of claim 5, in which said bracket further includes an attachment end portion at the end of said bracket opposite said arm, said attachment end portion extending lengthwise of said rail member and having a face opposed to and conforming generally in shape to the opposed surface of said rail member, and means rigidly interconnecting said attachment end portion and rail member.

8. The apparatus of claim 7, in which said face of said attachment end portion is concavely curved for maximum area contact with a substantially circular cross section rail member.

9. The apparatus of claim 7 in which said attachment end portion comprises a curved shell having its concave face opposing said rail member, said attachment end portion further including a semicircular cross section adapter with a convex face complementary to and in substantial area contact with said concave face of said shell and an opposite flat face, said rail member being of substantially rectangular cross section with a side face in wide area contact with said flat face of said adapter.

10. A urinary drainage bag support for supporting a urinary drainage bag on an item of patient support furniture, such as a chair, of the kind having a patient support surface and a rail member extending longitudinally beneath the patient support surface, said urinary drainage bag support comprising:

a bracket having a portion securable fixedly to said rail member, said bracket further including an elongate tongue extending transversely from said fixedly securable portion of the bracket to underlie said patient support surface;

a substantially horizontal arm pivotally supported on and extending from said tongue and adapted to lie beneath said patient support surface wherein said bracket and arm have respective axially opposed end portions and including a substantially vertically extending pivot pin pivotally securing said arm on said bracket, said end portions of said bracket and arm having means defining two sets of mutually opposed abutment surfaces located to interfere at spaced points along the path of pivotal movement of said arm for positively limiting the swing of said arm to less than half a circle;

an envelope pendently supported on said arm and opening upwardly to receive and support therein the urinary drainage bag, said envelope thus being pivoted with respect to said tongue for movement between use and stowed positions defined by said abutment surfaces.

11. The apparatus of claim 10, in which said abutment surface defining means include an axially protruding skirt means on said end portion of said bracket, said skirt means being disposed along the path of pivotal movement of said arm and being of circumferential extent to limit the swing of said arm to about a quarter circle.

12. The apparatus of claim 11, in which said fixedly securable portion of said bracket connects to and supports said end portion of said bracket through said elongate tongue which tongue angles downwardly and transversely inwardly away from said rail member to locate said arm inboard of the edge of and spaced below the level of said patient support surface, said tongue being a platelike member for disposition in a vertical plane with a first substantially upstanding edge fixed to said bracket fixedly securable portion, the latter extending transversely of said platelike tongue and facing concavely away from said first edge, said platelike tongue having a second substantially upstanding edge offset downward and laterally from said first edge and fixed to said end portion, the latter comprising a substantially cylindrical upstanding member, said platelike tongue having top and bottom edges sloped downward from said fixedly securable portion to said upstanding member.

* * * * *